(12) United States Patent
Harding

(10) Patent No.: US 7,519,154 B2
(45) Date of Patent: Apr. 14, 2009

(54) SYSTEMS AND METHODS FOR USING A CRYSTALLINITY OF A SUBSTANCE TO IDENTIFY THE SUBSTANCE

(75) Inventor: Geoffrey Harding, Hamburg (DE)

(73) Assignee: GE Security, Inc., Bradenton, FL (US)

( * ) Notice: Subject to any disclaimer, the term of this patent is extended or adjusted under 35 U.S.C. 154(b) by 254 days.

(21) Appl. No.: 11/504,395

(22) Filed: Aug. 15, 2006

(65) Prior Publication Data

US 2009/0060133 A1     Mar. 5, 2009

(51) Int. Cl.
    *G01T 1/36*     (2006.01)
(52) U.S. Cl. .......................................... 378/83; 378/73
(58) Field of Classification Search .................... 378/73, 378/83, 70, 71, 82
    See application file for complete search history.

(56) References Cited

U.S. PATENT DOCUMENTS

| 4,686,631 | A | 8/1987 | Ruud |  |
|---|---|---|---|---|
| 5,414,747 | A | 5/1995 | Ruud et al. |  |
| 2004/0013231 | A1* | 1/2004 | He et al. | 378/73 |
| 2004/0103130 | A1* | 5/2004 | Ivanisevic et al. | 708/200 |

FOREIGN PATENT DOCUMENTS

EP     0462658 A2    12/1991

OTHER PUBLICATIONS

International Search Report for application EP 07113412, dated Nov. 22, 2007.
Harding Geoffery: "Effective density and atomic number determined from diffraction profiles" Proc Spie Int Soc Opt Eng; Proceedings of Spie—The International Society for Optical Engineering; Hard X-Ray and Gamma-Ray Detector Physics and Penetrating Radiation Systems VIII, vol. 6319, Aug. 30, 2006, pp. 631910-1 to 631910-9.
Gok A et al.: "X-ray diffraction studies and DC electrical conductivity of poly(2-halogenanilines) and their composites with polyfuran" Materials Letters, North Holland Publishing Company. Amsterdam, NL, vol. 59, No. 1, Jan. 2005, pp. 80-84.
Barroso R C et al.: "Angle-dispersive diffraction with synchrotron radiation at Laboratorio Nacional de Luz Sncrotron (Brazil): potential for use in biomedical imaging" Applied Radiation and Isotopes, Elsevier, Oxford, GB, vol. 53, No. 4-5, Nov. 2000, pp. 717-724.
http://www.kratos.com/XRD/Apps/pcent.html; "Percentage Crystallinity Determination by X-Ray Diffraction"; XRD-6000 Application Brief; Kratos Analytical A Shimadzu Group Company; 1999; pp. 1-5.
Committee on Commerical Aviation Security; "Detection of Explosives for Commerical Aviation Security"; Publication NMAB-471 National Academy Press 1993, pp. 8, 9, and 12.
A. M. Hindeleh and D. J. Johnson; "The Resolution of Multipeak Data in Fibre Science"; J. Phys. D: Appl. Phys., 1971, vol. 4. Printed in Great Britain, pp. 259-263.

(Continued)

*Primary Examiner*—Hoon Song
(74) *Attorney, Agent, or Firm*—Eugene Hyun, Esq.; Armstrong Teasdale LLP

(57) ABSTRACT

A method for naming a substance is described. The method includes using a crystallinity of the substance to name the substance.

20 Claims, 10 Drawing Sheets

OTHER PUBLICATIONS http://www-cms.llnl.tgov/s-t/mol_mod.html; "Molecular Modeling of Aging Process"; Jan. 26, 2005, UCRL-WEB-151939, pp. 1-6.
U.S. Appl. No. 11/434,431, filed May 15, 2006, Geoffrey Harding.
U.S. Appl. No. 11/504,263, filed Aug. 15, 2007, Geoffrey Harding.
U.S. Appl. No. 11/498,114, filed Aug. 2, 2006, Geoffrey Harding.
U.S. Appl. No. 11/498,113, filed Aug. 2, 2006, Geoffrey Harding.
U.S. Appl. No. 11/484,186, filed Jul. 11, 2006, Geoffrey Harding.
U.S. Appl. No. 11/416,526, filed May 3, 2006, Geoffrey Harding.
U.S. Appl. No. 11/541,716, filed Sep. 29, 2006, Geoffrey Harding.
U.S. Appl. No. 11/531,019, filed Sep. 12, 2006, Geoffrey Harding.
U.S. Appl. No. 11/434,486, filed May 15, 2006, Geoffrey Harding.
U.S. Appl. No. 11/434,291, filed May 15, 2006, Geoffrey Harding.
U.S. Appl. No. 11/531,037, filed May 12, 2006, Geoffrey Harding.
Hubbell, J.H., Veigele, W.J., Briggs, E.A., Brown, R.T., Cromer, D.T., Howerton, R.J., "Atomic Form Factors, Incoherent Scattering Functions and Photon Scattering Cross-sections," Journal of Physics and Chemical Reference Data, vol. 4, No. 3, pp. 471-538 (1975).
Hubbell, J.H., Veigele, W.J., Briggs, E.A., Brown, R.T., Cromer, D.T., Howerton, R.J., "Erratum; Atomic Form Factors, Incoherent Scattering Functions, and Photon Scattering Cross Sections," Journal of Physics and Chemical Reference Data, vol. 6, pp. 615-616 (1977).
Schlomka et al., "Coherent Scatter Computer Tomography—A Novel Medical Imaging Technique," Physics of Medical Imaging, Proceedings of SPIE—vol. 5030, pp. 256-265 (2003).
Rabiej M., "Determination of the Degree of Crystallinity of Semicrystalline Polymers by Means of the 'OptiFit' Computer Software," Polimery 6, pp. 423-427 (2002).
"Percentage Crystallinity Determination by X-Ray Diffraction," XRD-6000 Application Brief, Kratos Analytical—A Shimadzu Group Company, pp. 1-5 (1999).
A.M. Hindeleh and D. J. Johnson, "The Resolution of Multipeak Data in Fibre Science," J. Phys. D: Appl. Phys., vol. 4. Printed in Great Britain, pp. 259-263 (1971).

* cited by examiner

SYSTEMS AND METHODS FOR USING A CRYSTALLINITY OF A SUBSTANCE TO IDENTIFY THE SUBSTANCE

BACKGROUND OF THE INVENTION

This invention relates generally to imaging systems and more particularly to systems and methods for using a crystallinity of a substance to identify the substance.

The events of Sep. 11, 2001 instigated an urgency for more effective and stringent screening of airport baggage. The urgency for security expanded from an inspection of carry-on bags for knives and guns to a complete inspection of checked bags for a range of hazards with particular emphasis upon concealed explosives. X-ray imaging is a widespread technology currently employed for screening. However, existing x-ray baggage scanners, including computed tomography (CT) systems, designed for detection of explosive and illegal substances are unable to discriminate between harmless materials in certain ranges of density and threat materials like plastic explosive.

A plurality of identification systems based on a plurality of x-ray diffraction (XRD) techniques provide an improved discrimination of materials compared to that provided by the x-ray baggage scanners. Whenever x-rays encounter a crystalline material, a plurality of regularly spaced atoms of the crystalline material diffract some of the x-rays to generate a diffraction pattern. The diffraction pattern is indicative of a crystal structure of the crystalline material, and various properties of the crystalline material can be analyzed based upon particular features of the pattern. The XRD identification systems measure a plurality of d-spacings between a plurality of lattice planes of micro-crystals in the crystalline material.

However, the XRD identification systems for explosives detection and baggage scanning help identify the d-spacings, which identify the crystalline material with a limited confidence. The identification of the crystalline material to with the limited confidence may result in a false alarm problem for some classes of substances. There are certain types of explosives in which an explosive component cannot be identified by the XRD identification systems and the lack of identification leads to a high false alarm rate.

BRIEF DESCRIPTION OF THE INVENTION

In one aspect, a method is described. The method includes using a crystallinity of a substance to name the substance.

In another aspect, a processor is described. The processor is configured to identify a substance based on a crystallinity of the substance.

In yet another aspect, an imaging system is described. The imaging system includes a source configured to generate energy, a detector configured to detector a portion of the energy, and a processor coupled to the detector and configured to name a substance based on a crystallinity of the substance.

DETAILED DESCRIPTION OF THE INVENTION

Figure 1:
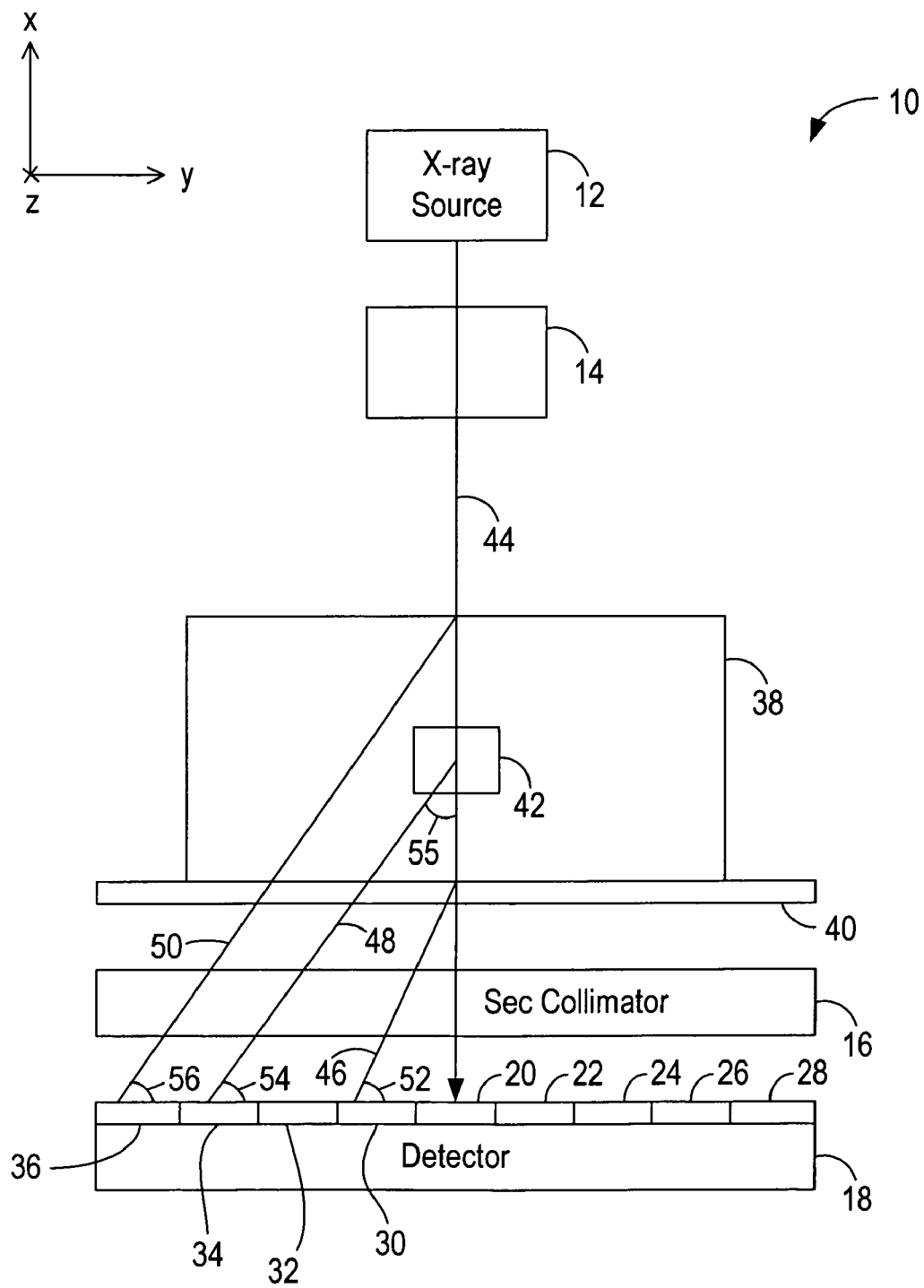
FIG. 1 is a block diagram of a system for using a crystallinity of a substance to identify the substance.

FIG. 1 is a block diagram of a system 10 for using a crystallinity of a substance to identify the substance. System 10 includes an x-ray source 12, a primary collimator 14, a secondary collimator (Sec collimator) 16, and a detector 18. Detector 18 includes a central detector element 20 or a central detector cell for detecting primary radiation. Detector 18 also includes a plurality of detector cells or detector elements 22, 24, 26, 28, 30, 32, 34, and 36 for detecting coherent scatter. Detector 18 includes any number, such as, ranging from and including 256 to 1024, of detector elements. A container 38 is placed on a support 40 between x-ray source 12 and detector 18. Examples of container 38 include a bag, a box, and an air cargo container. Examples of x-ray source 12 include a polychromatic x-ray tube. Container 38 includes a substance 42. Examples of substance 42 include an organic explosive, an amorphous substance having a crystallinity of less than twenty five percent, a quasi-amorphous substance having a crystallinity at least equal to twenty-five percent and less than fifty percent, and a partially crystalline substance having a crystallinity at least equal to fifty percent and less than one-hundred percent. Examples of the amorphous, quasi-amorphous, and partially crystalline substances include a gel explosive, a slurry explosive, an explosive including ammonium nitrate, and a special nuclear material. Examples of the special nuclear material include plutonium and uranium. Examples of support 40 include a table and a conveyor belt. An example of detector 18 includes a segmented detector fabricated from Germanium.

X-ray source 12 emits x-rays in an energy range, which is dependent on a voltage applied by a power source to x-ray source 12. Using primary collimator 14, a primary beam 44, such as a pencil beam, is formed from the x-rays generated. Primary beam 44 passes through container 38 arranged on support 40 to generate scattered radiation, such as a plurality of scattered rays 46, 48 and 50. Primary beam 44 passes through substance 42 to output scatter ray 48. Underneath support 40, there is arranged detector 18, which measures an intensity of primary beam 44 and photon energy of the scattered radiation. Detector 18 measures the scattered radiation in an energy-sensitive manner by outputting a plurality of electrical output signals linearly dependent on a plurality of energies of x-ray quanta detected from within primary beam 44 and the scattered radiation.

Detector elements 20, 22, 24, 26, 28, 30, 32, 34, and 36 are geometrically arranged so that an incident angle of the scatter radiation detected by each detector element 20, 22, 24, 26, 28, 30, 32, 34, and 36 is constant. For example, an incident angle 52 at which scattered ray 46 is incident on detector element 30 is equal to an incident angle 54 at which scattered ray 48 is incident on detector element 34 and incident angle 54 is equal to an incident angle 56 at which scattered ray 50 is incident on detector element 36. As another example, scattered ray 46 is parallel to scattered rays 48 and 50. Central detector element 20 measures an energy or alternatively an intensity of primary beam 44 after primary beam 44 passes through container 38. Detector elements 22, 24, 26, 28, 30, 32, 34, and 36 separately detect the scattered radiation received from container 38. A scatter angle 55 is formed between scattered ray 48 and primary beam 44.

Secondary collimator 16 is located between support 40 and detector 18. Secondary collimator 16 includes a number of collimator elements, such as sheets, slits, or laminations, to ensure that the scatter radiation arriving at detector 18 have a constant scatter angle with respect to primary beam 44 and that a position of detector 18 permits a depth in container 38 at which the scatter radiation originated to be determined. The number of collimator elements provided is equal to or alternatively greater than a number of detector elements 20, 22, 24, 26, 28, 30, 32, 34, and 36 and the collimator elements are arranged such that the scattered radiation between neighboring collimator elements each time is incident on one of the detector elements 22, 24, 26, 28, 30, 32, 34, and 36. The collimator elements are made of a radiation-absorbing material, such as, a copper alloy or a silver alloy. In one embodiment employing a fan-beam geometry, a plurality of origination points of the scattered radiation exist within container 38, and the scatter radiation is detected by the detector elements 22, 24, 26, and 28, aligned in a first direction and detector elements 30, 32, 34, and 36 aligned in a second direction opposite to and parallel to the first direction. Detector 18 detects the scattered radiation to generate a plurality of electrical output signals. In an alternative embodiment, system 10 does not include primary and secondary collimators 14 and 16.

Figure 2:
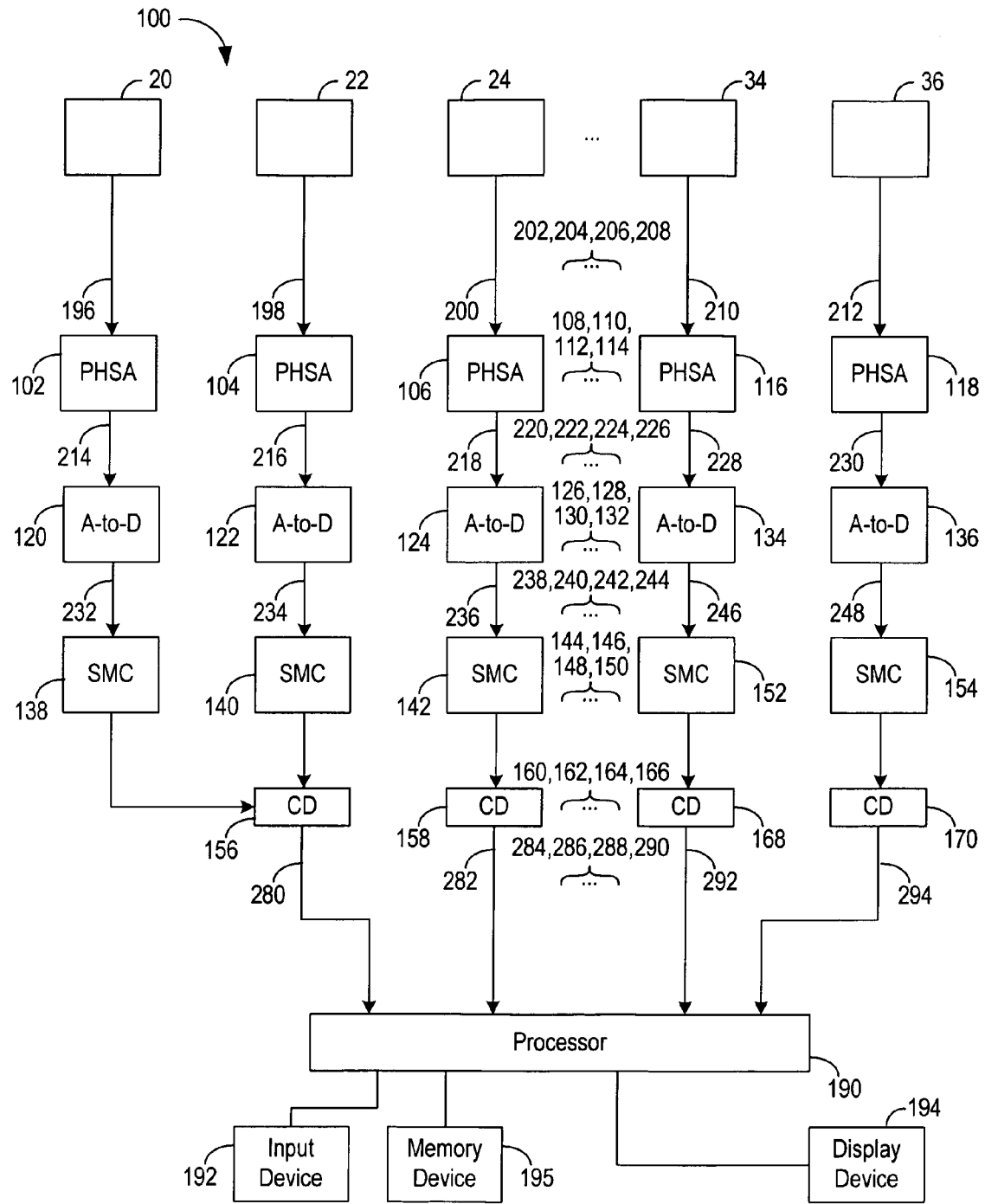
FIG. 2 is a block diagram of an embodiment of the system of FIG. 1.

FIG. 2 is a block diagram of an embodiment of a system 100 for using a crystallinity of a substance to identify the substance. System 100 includes central detector element 20, detector elements 22, 24, 26, 28, 30, 32, 34, and 36, a plurality of pulse-height shaper amplifiers (PHSA) 102, 104, 106, 108, 110, 112, 114, 116, and 118, a plurality of analog-to-digital (A-to-D) converters 120, 122, 124, 126, 128, 130, 132, 134, and 136, a plurality of spectrum memory circuits (SMCs) 138, 140, 142, 144, 146, 148, 150, 152, and 154 allowing pulse height spectra to be acquired, a plurality of correction devices (CDs) 156, 158, 160, 162, 164, 166, 168, and 170, a processor 190, an input device 192, a display device 194, and a memory device 195. As used herein, the term processor is not limited to just those integrated circuits referred to in the art as a processor, but broadly refers to a computer, a microcontroller, a microcomputer, a programmable logic controller, an application specific integrated circuit, and any other programmable circuit. The computer may include a device, such as, a floppy disk drive or CD-ROM drive, for reading data including the methods for using a crystallinity of a substance to identify the substance from a computer-readable medium, such as a floppy disk, a compact disc-read only memory (CD-ROM), a magneto-optical disk (MOD), or a digital versatile disc (DVD). In another embodiment, processor 190 executes instructions stored in firmware. Examples of display device 194 include a liquid crystal display (LCD) and a cathode ray tube (CRT). Examples of input device 192 include a mouse and a keyboard. Examples of memory device 195 include a random access memory (RAM) and a read-only memory (ROM). An example of each of correction devices 156, 158, 160, 162, 164, 166, 168, and 170 include a divider circuit. Each of spectrum memory circuits 138, 140, 142, 144, 146, 148, 150, 152, and 154 include an adder and a memory device, such as a RAM or a ROM.

Central detector element 20 is coupled to pulse-height shaper amplifier 102, and detector elements 22, 24, 26, 28, 30, 32, 34, and 36 are coupled to pulse-height shaper amplifiers 104, 106, 108, 110, 112, 114, 116, and 118, respectively. Central detector element 20 generates an electrical output signal 196 by detecting primary beam 44 and detector elements 22, 24, 26, 28, 30, 32, 34, and 36 generate a plurality of electrical output signals 198, 200, 202, 204, 206, 208, 210, and 212 by detecting the scattered radiation. For example, detector element 22 generates electrical output signal 198 for each scattered x-ray photon incident on detector element 22. Each pulse-height shaper amplifier amplifies an electrical output signal received from a detector element. For example, pulse-height shaper amplifier 102 amplifies electrical output signal 196 and pulse-height shaper amplifier 104 amplifies electrical output signal 198. Pulse-height shaper amplifiers 102, 104, 106, 108, 110, 112, 114, 116, and 118 have a gain factor determined by processor 190.

An amplitude of an electrical output signal output from a detector element is proportional to an integrated intensity of an x-ray quantum that is detected by the detector element to generate the electrical output signal. For example, an amplitude of electrical output signal 196 is proportional to an integrated intensity of an x-ray quantum in primary beam 44 detected by detector element 20. On the other hand, an amplitude of electrical output signal 198 is proportional to an integrated intensity of an x-ray quantum within the scattered radiation that is detected by central detector element 22.

A pulse-height shaper amplifier generates an amplified output signal by amplifying an electrical output signal generated from a detector element. For example, pulse-height shaper amplifier 102 generates an amplified output signal 214 by amplifying electrical output signal 196 and pulse-height shaper amplifier 104 generates an amplified output signal 216 by amplifying electrical output signal 198. Similarly, a plurality of amplified output signals 218, 220, 222, 224, 226, 228, and 230 are generated. An analog-to-digital converter converts an amplified output signal from an analog form to a digital form to generate a digital output signal. For example, analog-to-digital converter 120 converts amplified output signal 214 from an analog form to a digital format to generate a digital output signal 232. Similarly, a plurality of digital output signals 234, 236, 238, 240, 242, 244, 246, and 248 are generated by analog-to-digital converters 122, 124, 126, 128, 130, 132, 134, and 136, respectively. A digital value of a digital output signal generated by an analog-to-digital converter represents an amplitude of energy or alternatively an amplitude of intensity of a pulse of an amplified output signal. Each pulse is generated by an x-ray quantum, such as an x-ray photon. For example, a digital value of digital output signal 234 output by analog-to-digital converter 122 is a value of an amplitude of a pulse of amplified output signal 216.

An adder of a spectrum memory circuit adds a number of pulses in digital output signals. For example, when analog-to-digital converter 122 converts a pulse of amplified output signal 216 into digital output signal 234 to determine an amplitude of the pulse of amplified output signal 216, an adder within spectrum memory circuit 140 increments, by one, a value within a memory device of spectrum memory circuit 140. Accordingly, at an end of an x-ray examination of substance 42, a memory device within a spectrum memory circuit stores a number of x-ray quanta detected by a detector element. For example, a memory device within spectrum memory circuit 142 stores a number of x-ray photons detected by detector element 24 and each of the x-ray photons has an amplitude of energy or alternatively an amplitude of intensity that is determined by analog-to-digital converter 124.

A correction device receives a number of x-ray quanta that have a range of energies and are stored within a memory device of one of spectrum memory circuits 140, 142, 144, 146, 148, 150, 152, and 154, and divides the number by a number of x-ray quanta having the range of energies received from a memory device of spectrum memory circuit 138. For example, correction device 156 receives a number of x-ray photons having a range of energies from a memory device of spectrum memory circuit 140, and divides the number by a number of x-ray photons having the range received from a memory device of spectrum memory circuit 138. Each correction device outputs a correction output signal that represents a range of energies within x-ray quanta received by a detector element. For example, correction device 156 outputs a correction output signal 280 representing an energy spectrum or alternatively an intensity spectrum within x-ray quanta detected by detector element 22. As another example, correction device 158 outputs correction output signal 282 representing an energy spectrum within x-ray quanta detector element 24. Similarly, a plurality of correction output signals 284, 286, 288, 290, 292, and 294 are generated by correction devices 160, 162, 164, 166, 168, and 170, respectively.

Processor 190 receives correction output signals 280, 282, 284, 286, 288, 290, 292, and 294 to generate a momentum transfer x, measured in inverse nanometers ($nm^{-1}$), from an energy spectrum r(E) of energy E of x-ray quanta within the scattered radiation detected by detector 18. Processor 190 generates the momentum transfer x by applying $$x = (E/hc)\sin(\theta/2) \quad (1)$$

where c is a speed of light, h is Planck's constant, $\theta$ represents a constant scatter angle of x-ray quanta of the scattered radiation detected by the detector 18. Processor 190 relates the energy E to the momentum transfer x by equation (1). Mechanical dimensions of the secondary collimator 16 define the scatter angle $\theta$. The secondary collimator 16 restricts the scatter radiation that does not have the angle $\theta$. Processor 190 receives the scatter angle $\theta$ from a user via input device 192 to generate the momentum transfer x by applying equation (1). Processor 190 generates a diffraction profile D(x) from correction output signals 280, 282, 284, 286, 288, 290, 292, and 294.

It is noted that a number of pulse-height shaper amplifiers 102, 104, 106, 108, 110, 112, 114, 116, and 118 changes with a number of detector elements 20, 22, 24, 26, 28, 30, 32, 34, and 36. For example, five pulse-height shaper amplifiers are used for amplifying signals received from five detector elements. As another example, four pulse-height shaper amplifiers are used for amplifying signals received from four detector elements. Similarly, a number of analog-to-digital converters 120, 122, 124, 126, 128, 130, 132, 134, and 136 changes with a number of detector elements 20, 22, 24, 26, 28, 30, 32, 34, and 36 and a number of spectrum memory circuits 138, 140, 142, 144, 146, 148, 150, 152, and 154 changes with the number of detector elements 20, 22, 24, 26, 28, 30, 32, 34, and 36.

Figure 3:
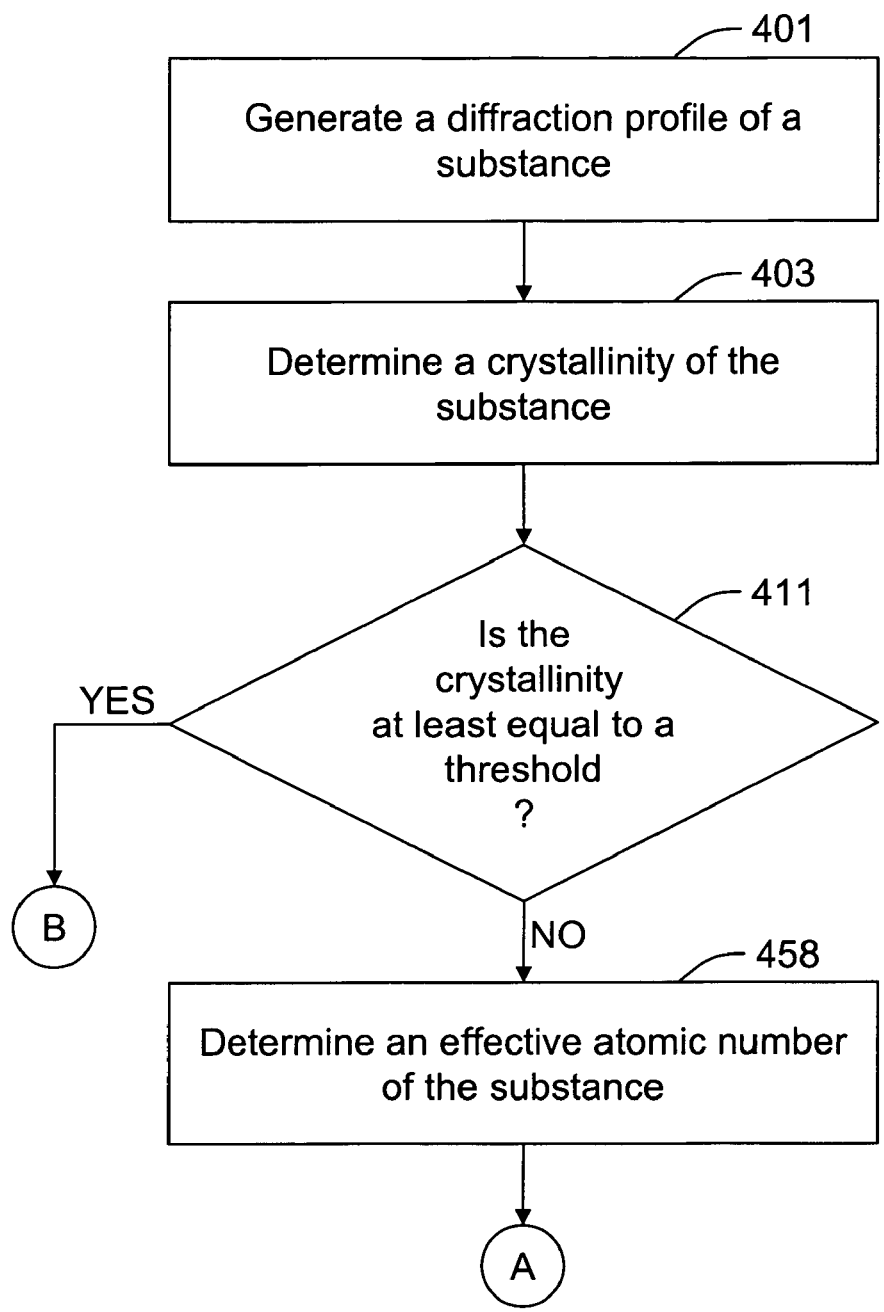
FIG. 3 is a flowchart of an embodiment of a method for using a crystallinity of a substance to identify the substance.
Figure 4:
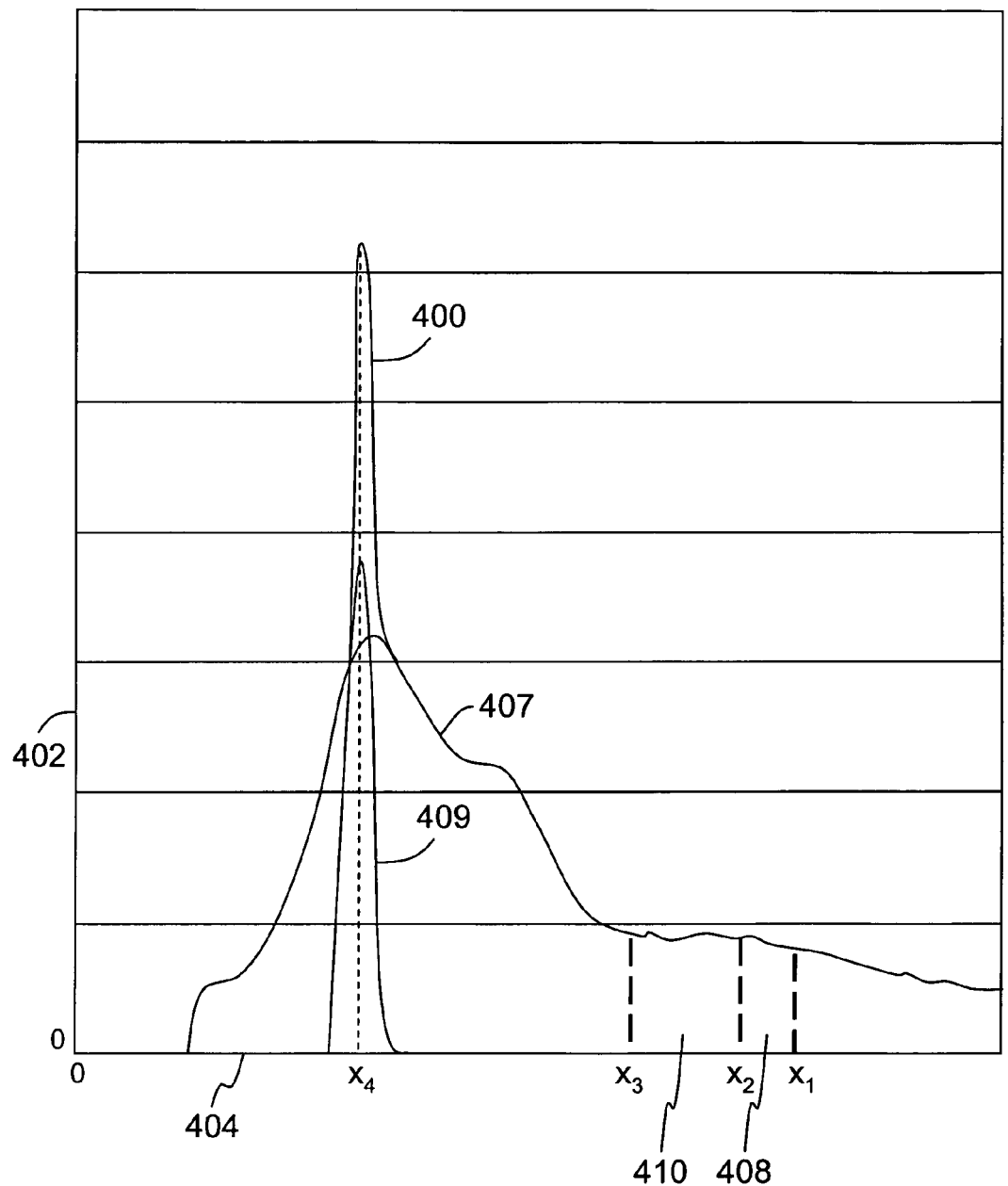
FIG. 4 shows a diffraction profile generated by a processor of the system of FIG. 2.
Figure 5:
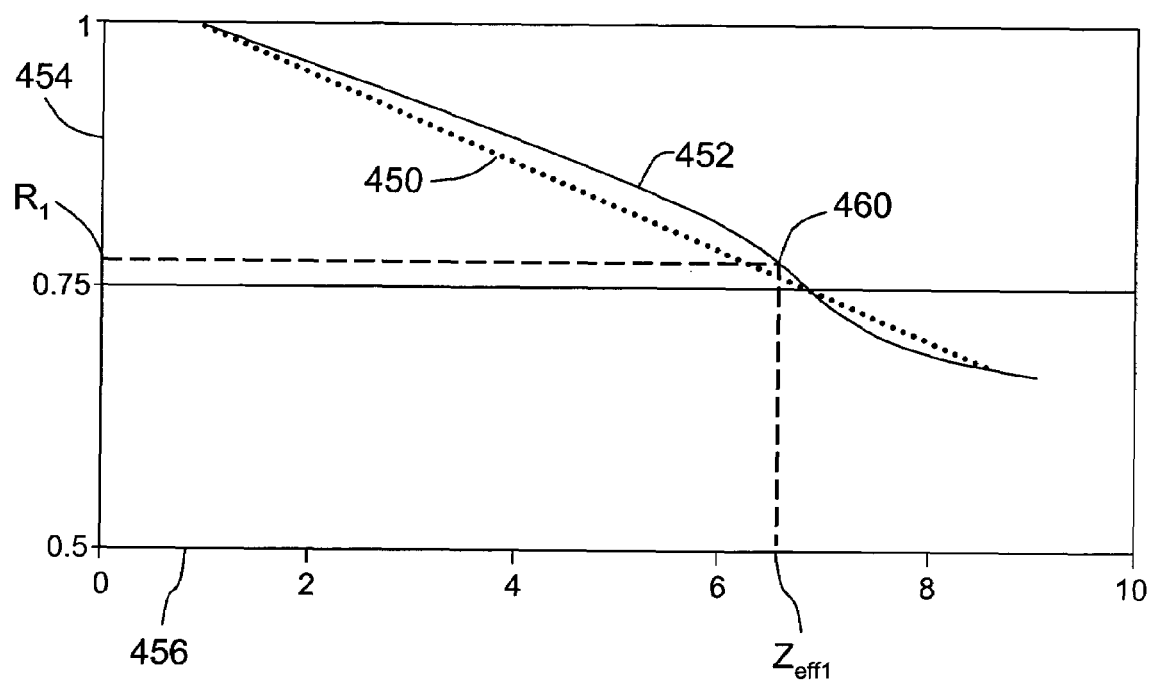
FIG. 5 shows a dotted line and a solid curve generated by the processor of the system of FIG. 2.

FIG. 3 is a flowchart of an embodiment of a method for using a crystallinity of a substance to identify the substance, FIG. 4 shows a graph 400 generated 401 by processor 190, and FIG. 5 shows a dotted line 450 and a solid curve 452 generated by processor 190. Graph 400 is an example of the diffraction profile D(x). Graph 400 is a histogram having a plurality of intensity values at a plurality of momentum transfer values, such as $x_1$, $x_2$, and $X_3$, of the momentum transfer x. As an example, when an operating voltage of x-ray source 12 is 160 kilovolts, processor 190 calculates, by applying equation 1, an energy value $E_1$ of the energy E to be 160 kilo electronVolts (keV), calculates, by applying equation 1, an energy value $E_2$ of the energy E to be 140 keV, and calculates, by applying equation 1, an energy value $E_3$ of the energy value E to be photon energy 120 keV. In the example, the photon energy values $E_1$, $E_2$, and $E_3$ correspond, through equation 1, to $x_1$ of four inverse nanometers, $x_2$ of 3.5 inverse nanometers, and to $x_3$ of three inverse nanometers, respectively. Graph 400 represents a histogram of a number of x-ray photons detected by detector 18 versus the momentum transfer x of the x-ray photons. A number of photons detected by detector 18 is plotted along an ordinate 402 and the momentum transfer x is plotted along an abscissa 404. As an example, abscissa 404 extends from and includes zero inverse nanometers to at most 10 inverse nanometers. An example of a total number of bins of numbers of x-ray photons plotted on ordinate 402 lies between 64 and 1024. An example of a number of x-ray photons detected by detector 18 per examination lies between 1000 and 100,000.

Graph 400 ranging from $x \geq 3$ $nm^{-1}$ is dominated by coherent scatter from free atoms of substance 42. In a tip region, extending from $x_1$ to $x_3$, of graph 400, an intensity of the scattered radiation is proportional to a product of an effective density of substance 42 and a power, such as ranging between 2.5 and 3.5, of an effective atomic number of substance 42.

Processor 190 determines 403 a crystallinity of substance 42 from the diffraction profile D(x). Processor 190 applies a Fourier transform to the diffraction profile D(x) to transform the diffraction profile D(x) from a momentum transfer domain to a frequency domain. In the frequency domain, an amorphous portion of substance 42 has a plurality of amorphous frequencies that are different than a plurality of crystalline frequencies of a crystalline portion of substance 42. The Fourier transform possesses a frequency band in which a plurality of contributions or amplitudes of peaks representing a crystalline nature of substance 42 are different than a plurality of contributions of peaks representing an amorphous nature of substance 42. Processor 190 applies an inverse Fourier transform to the frequency band to generate an amorphous momentum transfer domain curve 407 and a crystalline momentum transfer domain curve 409. Graph 400 is a sum of amorphous momentum transfer domain curve 407 and crystalline momentum transfer domain curve 409. An example of a computer software that generates an amorphous momentum transfer domain curve and a crystalline momentum transfer domain curve from a diffraction profile includes "OptiFit" computer software, described in Rabiej M, Determination of the Degree of Crystallinity of Semicrystalline Polymers by Means of the "OptiFit" Computer Software, POLIMERY 6, pages 423-427 (2002).

Processor 190 determines a crystalline area under crystalline momentum transfer domain curve 409 and determines a total area under graph 400. Processor 190 divides the crystalline area by the total area to determine 403 a crystallinity C of substance 42. An example of an application of the Fourier transform to determine a crystallinity from a diffraction profile is provided in Percentage Crystallinity Determination by X-ray Diffraction, XRD-6000 Application Brief, Kratos Analytical (1999). Processor 190 determines 411 whether the crystallinity C is at least equal to a threshold, such as ranging from and including 0.2 to 0.8. In the exemplary embodiment, if the crystallinity C is at least equal to the threshold, processor 190 follows a first process represented by path "B" in FIG. 3. If the crystallinity C is less than the threshold, processor 190 follows a second process represented by path "A" in FIG. 3.

An exemplary embodiment of the second process proceeds as follows. Upon determining that the crystallinity C is less than the threshold, processor 190 plots solid curve 452 that represents a theoretical relationship between a ratio of total free atom scatter cross-sections, referred to as total scatter cross-sections or cumulative scatter cross-sections, and an atomic number Z. As an example, processor 190 plots solid curve 452 from an example of the theoretical relationship mentioned in Hubbell, J. H., Veigele, W. J., Briggs, E. A., Brown, R. T., Cromer, D. T., Howerton, R. J., Atomic Form Factors, Incoherent Scattering Functions and Photon Scattering Cross-sections, Journal of Physics and Chemical Reference Data, Volume 4, page 471 (1975), Erratum: Atomic Form Factors, Incoherent Scattering Functions, and Photon Scattering Cross Sections, Journal of Physics and Chemical Reference Data, Volume 6, page 615 (1977). As another example, the theoretical relationship includes an atomic number value of oxygen as eight corresponding to a ratio of 0.68 of total scatter cross-sections calculated for oxygen. As yet another example, the theoretical relationship includes an atomic number value of carbon as six corresponding to a ratio of 0.73 of total scatter cross-sections calculated from carbon. As still another example, processor 190 calculates a ratio of a total scatter cross-section of hydrogen at the momentum transfer value $x_3$ and a total scatter cross-section of hydrogen at the momentum transfer value $x_2$, and plots the ratio on solid curve 452. As another example, processor 190 calculates a ratio of a total scatter cross-section of flourine at the momentum transfer value $x_2$ and a total scatter cross-section of flourine at the momentum transfer value $x_1$, and plots the ratio on solid curve 452. As yet another example, processor 190 calculates a ratio of a total scatter cross-section of carbon at the momentum transfer value $x_2$ and a total scatter cross-section of carbon at the momentum transfer value $x_1$, and plots the ratio on solid curve 452. Processor 190 generates dotted line 450 as a linear fit or linear regression to the theoretical relationship.

A plurality of ratios of total scatter cross-sections are plotted along an ordinate 454 and a plurality of atomic numbers Z are measured along an abscissa 456. For example, a plurality of atomic number values on dotted line 450 extend from an atomic number one of hydrogen to an atomic number nine of flourine and a plurality of ratios of total scatter cross-sections evaluated at momentum transfer values within a first set of regions of a plurality of bands 408 and 410 and total scatter cross-sections evaluated at momentum transfer values within a second set of regions of bands 408 and 410.

A number of x-ray photons that are scattered with momentum transfer values between $x_1$ and $x_2$ are represented within band 408 under graph 400. Processor 190 determines a cumulative number of x-ray photons within band 408 by cumulatively summing a number of photons between momentum transfer values $x_1$ and $x_2$ on abscissa 404. A number of x-ray photons that are scattered with momentum transfer values between $x_2$ and $X_3$ are located within band 410 under graph 400. Processor 190 determines a cumulative number of x-ray photons within band 410 by cumulatively summing a number of x-ray photons between momentum transfer values $x_2$ and $X_3$ on abscissa 404.

Processor 190 calculates a ratio of cumulative numbers of x-ray photons within bands 408 and 410. For example, processor 190 determines that $R_1$ is a ratio of a cumulative number of x-ray photons within band 408 to a cumulative number of x-ray photons within band 410. Processor 190 determines 458, by using the solid curve 452, an effective atomic number $Z_{eff}$ corresponding to a ratio of a cumulative number of x-ray photons within band 408 and a cumulative number of x-ray photons within band 410. As an example, processor 190 perpendicularly extends a horizontal line from the ratio $R_1$ to intersect solid curve 452 at an intersection point 460 and extends a line from intersection point 460 to perpendicularly intersect abscissa 456 at an effective atomic number value $Z_{eff1}$. Alternatively, processor 190 determines, by using the dotted line 450, the effective atomic number $Z_{eff}$ corresponding to a ratio of a cumulative number of x-ray photons within band 408 and a cumulative number of x-ray photons within band 410. As an example, processor 190 perpendicularly extends a horizontal line from the ratio $R_1$ to intersect dotted line 450 at an intersection point and extends a line from the intersection point to perpendicularly intersect abscissa 456 at an effective atomic number value $Z_{eff2}$.

Figure 6:
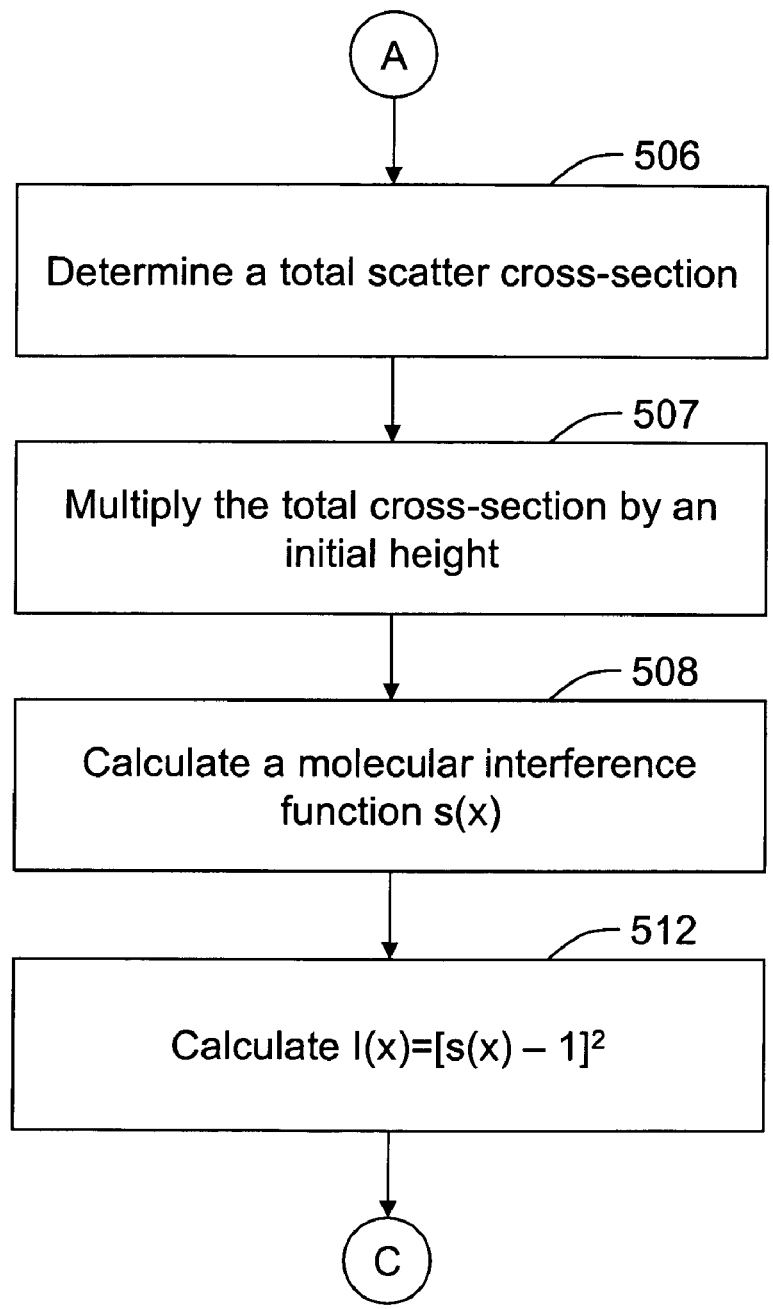
FIG. 6 is a continuation of the flowchart of FIG. 3.
Figure 7:
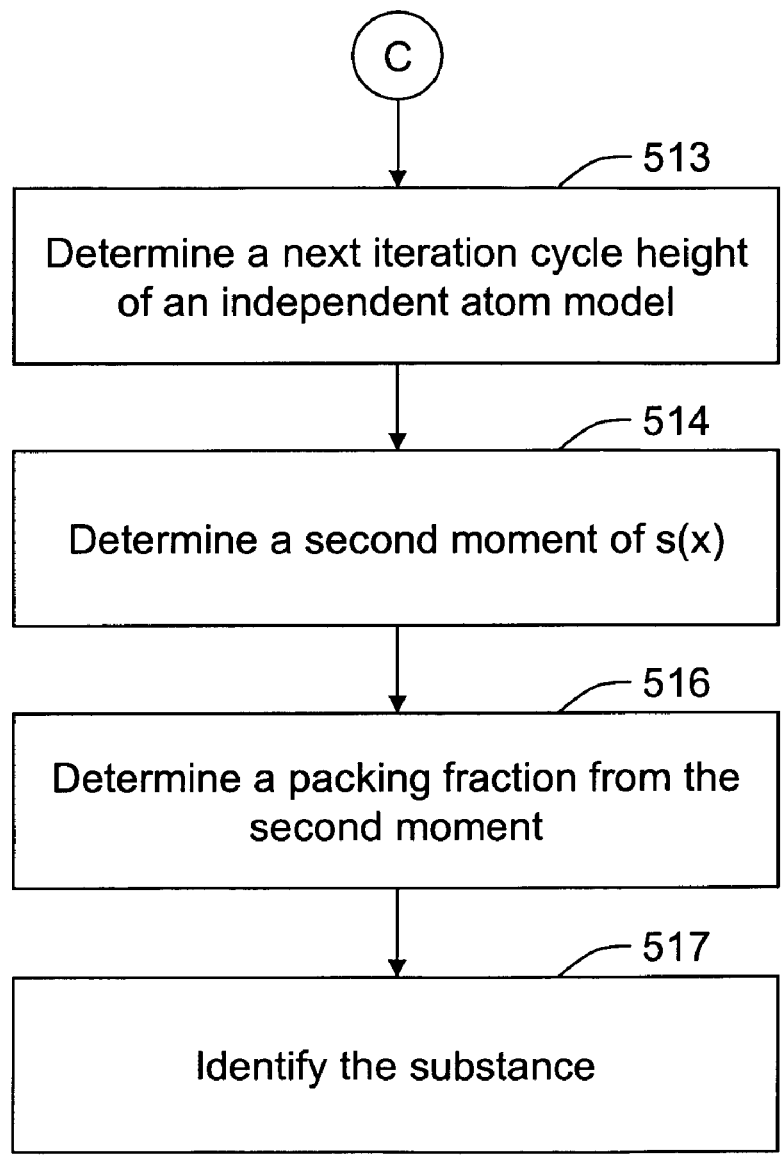
FIG. 7 is a continuation of the flowchart of FIG. 6.
Figure 8:
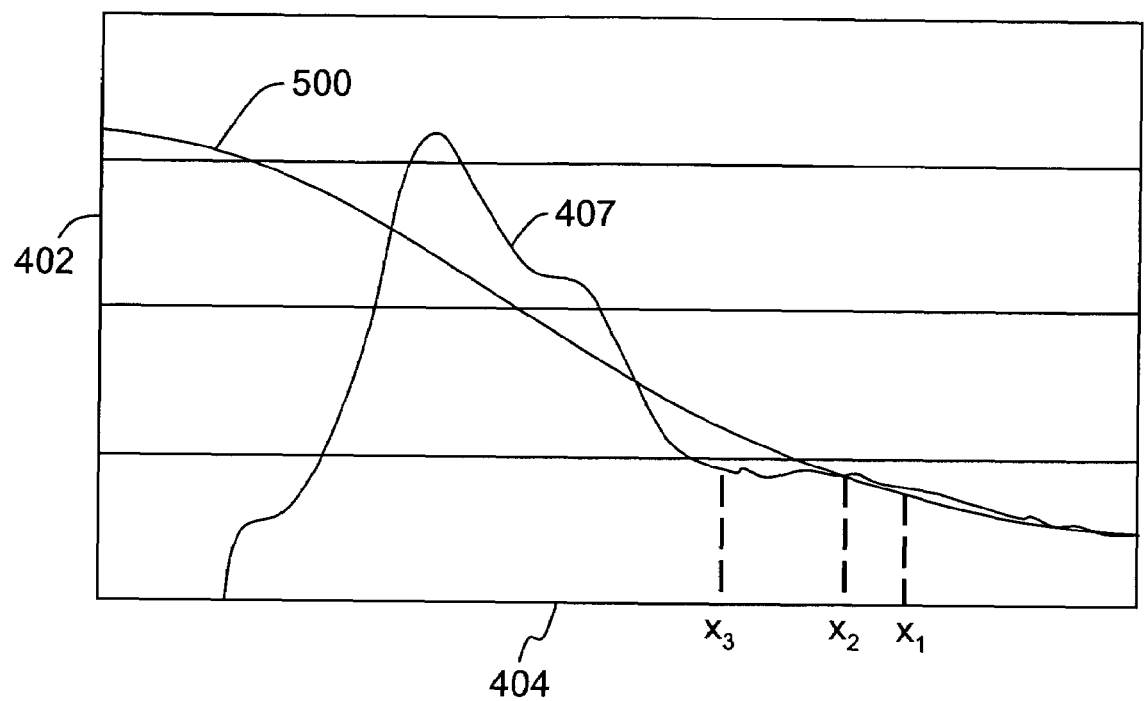
FIG. 8 shows an independent atom model curve generated by applying the method of FIGS. 3, 6 and 7.
Figure 9:
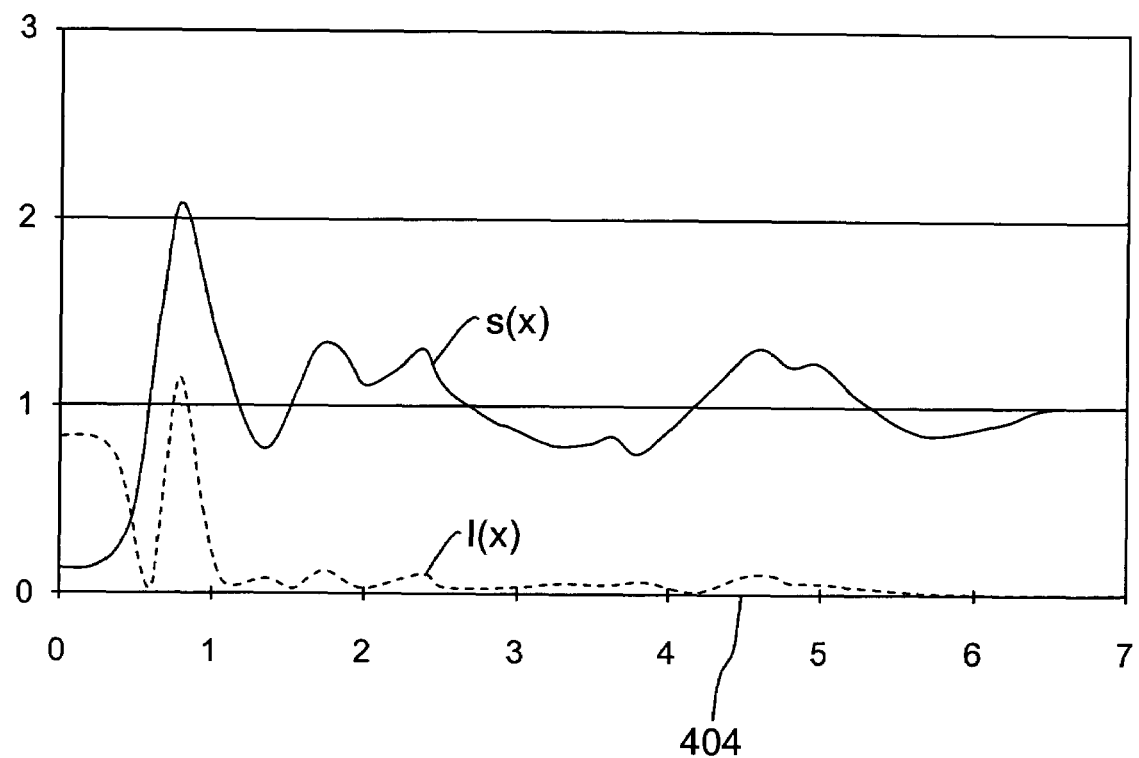
FIG. 9 shows an embodiment of a molecular transfer function and an embodiment of an approximation function generated by applying the method of FIGS. 3, 6 and 7.

FIGS. 6 and 7 are a flowchart of an embodiment of a method for using a crystallinity of a substance to identify the substance, FIG. 8 shows an embodiment of an independent atom model (IAM) curve 500 generated by processor 190, and FIG. 9 shows a plurality of embodiments of a plurality of graphs s(x) and I(x) generated by processor 190. The graph s(x) represents a molecular interference function and the graph I(x) represents an approximation function.

Processor 190 determines 506 a total scatter cross-section of IAM curve 500 from the effective atomic number $Z_{eff}$ that is illustrated in FIG. 5 and that is determined from the scattered radiation. For example, upon determining by processor 190 that the effective atomic number value $Z_{eff1}$ is a rational number, such as 6.3, processor 190 generates a weighted average of a plurality of LAM functions corresponding to neighboring atomic numbers six and seven. In the example, processor 190 generates the weighted average, such as ⅓[LAM(6)]+⅔[IAM(7)], where IAM(6) is a total scatter cross-section for carbon and IAM(7) is a total scatter cross-section for nitrogen. An example of the IAM functions corresponding to neighboring atomic numbers are available in Hubbell, J. H., Veigele, W. J., Briggs, E. A., Brown, R. T., Cromer, D. T., Howerton, R. J., Atomic Form Factors, Incoherent Scattering Functions and Photon Scattering Cross-sections, Journal of Physics and Chemical Reference Data, Volume 4, page 471 (1975), Erratum: Atomic Form Factors, Incoherent Scattering Functions, and Photon Scattering Cross Sections, Journal of Physics and Chemical Reference Data, Volume 6, page 615 (1977). The weighted average is an example of a total scatter cross-section, determined in 506, of IAM curve 500.

Alternatively, instead of generating the weighted average, upon determining by processor 190 that the effective atomic number value $Z_{eff1}$ is the rational number, processor 190 generates a closest total scatter cross-section of an IAM curve corresponding to an atomic number value, which is an integer closest to the rational number and plots, with respect to y-axis 402, the closest total scatter cross-section. In yet another alternative embodiment, instead of generating the weighted average, upon determining by processor 190 that the effective atomic number value $Z_{eff1}$ is the rational number, processor 190 generates a universal total scatter cross-section of an LAM curve by scaling the momentum transfer x of IAM curve 500 in FIG. 8. As an example, abscissa 404 in FIG. 8 is scaled by multiplying the momentum transfer x of LAM curve 500 with $0.02 Z_{eff1}+0.12$ to generate the universal total scatter cross-section.

Processor 190 multiplies 507 a total scatter cross-section, determined in 506, by an initial amplitude or an initial height to generate a first iteration cycle free atom curve. For example, processor 190 multiplies each value of a total scatter cross-section, determined in 506, with the initial height to generate the first iteration cycle free atom curve. Processor 190 receives the initial height from the user via input device 192. Processor 190 calculates 508 the molecular interference function s(x) by dividing a number of x-ray photons represented by amorphous momentum transfer curve 407 by the first iteration cycle free atom curve. As an example, processor 190 generates a molecular interference value $s_1(x)$ of the molecular interference function $s(x)$ by dividing a number of x-ray photons having the momentum transfer value $x_1$ that lies on amorphous momentum transfer curve 407 by a number of x-ray photons having the momentum transfer value $x_1$ that lies on the first iteration cycle free atom curve. As another example, processor 190 generates a molecular interference value $s_2(x)$ of the molecular interference function $s(x)$ by dividing a number of x-ray photons having the momentum transfer value $x_2$ that lies on amorphous momentum transfer curve 407 by a number of x-ray photons having the momentum transfer value $x_2$ that lies on the first iteration cycle free atom curve.

Processor 190 calculates 512 the approximation function $I(x)$ as $$I(x) = [s(x) - 1]^2 \quad (2)$$

Processor 190 determines 513 a next iteration cycle amplitude 1 mm or a next iteration cycle height of IAM curve 500 by minimizing an integral of $I(x)$ represented as $$\int_0^{x\max} I(x) dx \quad (3)$$

where $x_{max}$ is the largest value of x on abscissa 404 of amorphous momentum transfer curve 407 and IAM curve 500. For example, processor 190 determines the next iteration cycle height $I_{min}$ by selecting a minimum from a first and a second calculated value. Processor 190 determines the first calculated value by applying 507, 508, 512, and equation (3) to the initial height. Processor 190 determines the second calculated value by applying 507, 508, 512, and equation (3) to a changed height instead of the initial height. For example, processor 190 multiplies a total scatter cross-section, determined in 506, by the changed height to generate a second iteration cycle free atom curve, calculates the molecular interference function $s(x)$ by dividing a number of x-ray photons represented by amorphous momentum transfer curve 407 by the second iteration cycle free atom curve, calculates the approximation function $I(x)$ from equation (2), and generates the second calculated value by applying equation (3). Processor 190 generates the changed height by modifying, such as incrementing or decrementing, the initial height. As another example, processor 190 determines the next iteration cycle height $I_{min}$ by selecting a minimum from a plurality, such as three, of calculated values, such as the first calculated value, the second calculated value, and a third calculated value. Processor 190 generates the third calculated value in a similar manner in which first and second calculated values are generated. For example, processor 190 generates the third calculated value after incrementing or alternatively decrementing the changed height.

Processor 190 determines 514 a second moment X2S of $I(x)$ by applying $$X2S = \frac{\int_0^\infty x^2 I_{min}(x) dx}{\int_0^\infty I_{min}(x) dx} \quad (4)$$

Processor 190 determines 516 a packing fraction $\eta$ of substance 42 as being linearly proportional, such as equal, to the second moment X2S. The packing fraction $\eta$ is linearly proportional to the second moment X2S when substance 42 includes a plurality of identical hard spheres over a range of $\eta$ of amorphous materials relevant in explosive and contraband detection. An example of the linearly proportional relationship includes $$\eta = a(X2S) \quad (5)$$

where a is a coefficient received by processor 190 via input device 192 from the user, a ranges from and including 0.1 to 0.2.

Processor 190 identifies 517 substance 42 based on the crystallinity C of substance 42, the effective atomic number $Z_{eff}$ and the packing fraction $\eta$ of substance 42. For example, processor 190 retrieves, from a table stored within memory device 195, an identification, such as a name, of substance 42 as being graphite upon determining that the crystallinity C of substance 42 is equal to 0.2, the packing fraction $\eta$ of substance 42 is approximately equal to 0.5, such as ranging from and including 0.4 to 0.6, and the effective atomic number $Z_{eff}$ of substance 42 is equal to 6. In the example, the table includes that the crystallinity of 0.2, the packing fraction $\eta$ that is approximately equal to 0.5, and the effective atomic number of 6 corresponds to graphite. Processor 190 sends the crystallinity of 0.2, the packing fraction $\eta$ that is approximately equal to 0.5, and the effective atomic number of 6 to memory device 195 to determine, from the table, an identity of substance 42 as being graphite. A plurality of identities of substance 42 based on the crystallinity C of substance 42, the effective atomic number $Z_{eff}$ and the packing fraction 71 of substance 42 are pre-stored in the table within memory device 195 and the identities are pre-stored by the user via input device 192.

Figure 10:
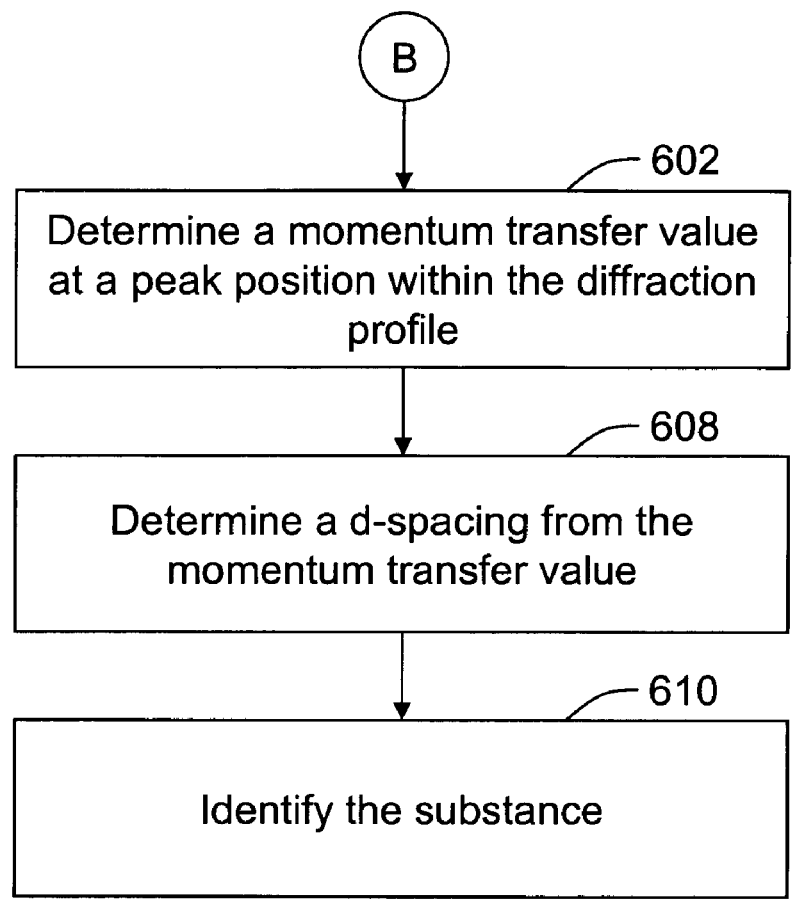
FIG. 10 is a continuation of the flowchart of FIG. 3.

Returning to FIG. 3, an exemplary embodiment of the first process represented by path "B" proceeds as follows. FIG. 10 is a flowchart of an embodiment of a method for using a crystallinity of a substance to identify the substance. Upon determining that the crystallinity C is at least equal to the threshold, processor 190 determines 602 a momentum transfer value at a peak position within the diffraction profile $D(x)$. For example, referring back to FIG. 4, processor 190 determines that graph 400 has a peak at a momentum transfer value of $x_4$. Processor 190 determines the peak position by generating a derivative of graph 400 with respect to the momentum transfer x and determining the momentum transfer value $x_4$ at which the derivative of graph 400 is zero. If processor 190 determines a plurality of momentum transfer values of the momentum transfer x at which the derivative of graph 400 is zero, processor 190 selects one of the momentum transfer values on graph 400 at which a number of x-ray photons on graph 400 is higher than the remaining numbers of x-ray photons that are plotted on graph 400 and that correspond to the remaining of the momentum transfer values on graph 400. For example, when processor 190 determines the momentum transfer value $x_4$ and a momentum transfer value $x_5$ are values on graph 400 at which the derivative of graph 400 is zero, processor 190 selects the momentum transfer value $x_4$ at which a number of x-ray photons, on graph 400, having the momentum transfer value $x_4$ are higher than a cumulative number of x-ray, on graph 400, photons having the momentum transfer value $x_5$. Processor 190 determines, in 608, d, which is a d-spacing or an interplanar atomic spacing between two adjacent planes of substance 42, from the momentum transfer value $x_4$ at the peak position by applying $$d = 1/(2x_4) \quad (6)$$

Each of the planes include a plurality of atoms of substance 42.

Processor 190 identifies 610 substance 42 based on the interplanar atomic spacing d of substance 42. For example, upon determining by processor 190 that substance 42 has d equal to 4.05 Angstroms, processor 190 retrieves from memory device 195 an identification, such as a name, of substance 42 as being aluminum. As another example, upon determining by processor 190 that substance 42 has d equal to 2.95 Angstroms, processor 190 retrieves from memory device 195 an identification of substance 42 as being titanium. A plurality of identities corresponding to a plurality of interplanar atomic spacings are pre-stored in the table in memory device 195 by the user via input device 192. When the crystallinity is at least equal to the threshold, the crystallinity C can be used to determine an age of substance 42. A plurality of ages of substance 42 corresponding to a plurality of crystallinity values are pre-stored in the table in memory device 195 by the user via input device 192. Processor 190 retrieves an age of substance 42 from table and the age corresponds to the crystallinity C.

Technical effects of the herein described systems and methods for using a crystallinity of a substance to identify the substance include determining whether to determine the interplanar atomic spacing d or to determine the packing fraction η and the effective atomic number $Z_{eff}$ based on the crystallinity C of substance 42. If the crystallinity C of substance 42 is at least equal to the threshold, processing time for performing 602, 608, and 610 is less than processing time for performing 458, 502, 506, 507, 508, 512, 513, 514, 516, and 517, which are performed when the crystallinity C is less than the threshold. Other technical effects include using the crystallinity C to identify substance 42. The crystallinity C also helps to determine an age of substance 42 from a time of making of substance 42. The crystallinity C changes with the age of substance 42.

While the invention has been described in terms of various specific embodiments, those skilled in the art will recognize that the invention can be practiced with modification within the spirit and scope of the claims.

What is claimed is:

1. A method for identifying a substance, said method comprising:
   determining a diffraction profile of the substance;
   determining a crystallinity from the diffraction profile;
   determining whether to apply a first process or a second process based on the crystallinity; and
   using one of the first process and the second process to identify the substance.

2. A method in accordance with claim 1, wherein the second process is longer than the first process.

3. A method in accordance with claim 1, wherein said determining whether to apply the first process or the second process comprises determining whether to apply the first process or the second process based on whether the crystallinity exceeds a threshold.

4. A method in accordance with claim 1 further comprising:
   determining whether the crystallinity is at least equal to a threshold; and
   applying the first process if the crystallinity is at least equal to the threshold.

5. A method in accordance with claim 1 further comprising:
   determining whether the crystallinity is at least equal to a threshold; and
   applying the second process if the crystallinity is less than the threshold.

6. A method in accordance with claim 1, wherein the first process comprises determining an interplanar atomic spacing of the substance.

7. A method in accordance with claim 1, wherein the second process comprises determining an effective atomic number of the substance.

8. A method in accordance with claim 1, wherein the second process comprises determining a packing fraction of the substance.

9. A processor configured to identify a substance, said processor further configured to:
   determine a diffraction profile of the substance;
   determine a crystallinity based on the diffraction profile;
   determine whether to apply a first process or a second process based on the crystallinity; and
   identify the substance using one of the first process and the second process.

10. A processor in accordance with claim 9 further configured to determine whether to apply the first process or the second process based on the crystallinity, wherein the second process is longer than the first process.

11. A processor in accordance with claim 9 further configured to determine whether to apply the first process or the second process based on whether the crystallinity exceeds a threshold.

12. A processor in accordance with claim 9 further configured to:
   determine whether the crystallinity is at least equal to a threshold; and
   apply the first process if the crystallinity is at least equal to the threshold.

13. A processor in accordance with claim 9 further configured to:
   determine whether the crystallinity is at least equal to a threshold; and
   apply the second process if the crystallinity is less than the threshold.

14. A processor in accordance with claim 9 further configured to:
   execute the first process to determine an interplanar atomic spacing of the substance.

15. An imaging system comprising:
   a source configured to generate energy;
   a detector configured to detect a portion of the energy; and
   a processor coupled to said detector, said processor configured to:
   determine a diffraction profile of a substance;
   determine a cystallinity of the substance based on the diffraction profile;
   determine whether to apply a first process or a second process based on the crystallinity; and
   identify the substance using one of the first process and the second process.

16. An imaging system in accordance with claim 15, wherein the second process is longer than the first process.

17. An imaging system in accordance with claim 15, wherein said processor is further configured to determine whether to apply the first process or the second process based on whether the crystallinity exceeds a threshold.

18. An imaging system in accordance with claim 15, wherein said processor is further configured to:
   determine whether the crystallinity is at least equal to a threshold; and
   apply the first process if the crystallinity is at least equal to the threshold.

19. An imaging system in accordance with claim 15, wherein said processor is further configured to:

determine whether the crystallinity is at least equal to a threshold; and
apply the second process if the crystallinity is less than the threshold.

20. A method for identifying a substance, said method comprising:
determining a diffraction profile of the substance;
determining a crystallinity from the diffraction profile;
determining an effective atomic number of the substance;
determining a packing fraction of the substance; and
identifying the substance based on the effective atomic number, the packing fraction, and the crystallinity.

* * * * *